(12) United States Patent
Carroll et al.

(10) Patent No.: US 7,208,599 B2
(45) Date of Patent: Apr. 24, 2007

(54) PREPARATION OF SUBSTITUTED ALKANESULFONATES FROM 2-HYDROXYALKANESULFONATES

(75) Inventors: Glenn T. Carroll, Norristown, PA (US); Gary S. Smith, Collegeville, PA (US); Gary E. Stringer, Birdsboro, PA (US)

(73) Assignee: Arkema Inc., Philadelphia, PA (US)

( * ) Notice: Subject to any disclaimer, the term of this patent is extended or adjusted under 35 U.S.C. 154(b) by 211 days.

(21) Appl. No.: 10/973,610

(22) Filed: Oct. 26, 2004

(65) Prior Publication Data

US 2006/0089509 A1 Apr. 27, 2006

Related U.S. Application Data

(60) Provisional application No. 60/503,263, filed on Sep. 16, 2003.

(51) Int. Cl.
 *C07D 241/04* (2006.01)
(52) U.S. Cl. ..................................................... 544/358
(58) Field of Classification Search ................. 544/358
 See application file for complete search history.

(56) References Cited

U.S. PATENT DOCUMENTS

| 4,080,315 A | 3/1978 | Login |
| 4,169,950 A | 10/1979 | Ferguson |
| 4,246,194 A | 1/1981 | Ferguson |
| 4,481,150 A | 11/1984 | Ishii et al. |
| 4,582,651 A | 4/1986 | Ishii et al. |

FOREIGN PATENT DOCUMENTS

| DE | 15289 | 8/1955 |
| DE | 1 151 149 | 7/1963 |
| DE | 84 394 | 9/1971 |
| FR | 1 529 883 | 5/1967 |
| FR | 2 041 439 | 4/1969 |
| FR | 2 270 241 | 5/1997 |
| GB | 815 167 | 6/1959 |
| GB | 1 381 828 | 1/1975 |
| GB | 1 503 280 | 3/1978 |
| JP | 04/360863 | 12/1992 |
| JP | 07/278097 | 10/1995 |
| WO | 99/41236 | 8/1999 |

OTHER PUBLICATIONS

Biochemistry Good, N.E. vol. 5, 1966 pp. 467-476.
Methods of Enzymology Chapter 3 of Photosynthesis, A San Pietro, Ed., vol. 23-24,69, 1971 pp. 53-68.
Shengwu Huaxue Yu Shenwu Wuli Jinzha vol. 37, pp. 44-46, 1981 Chemical Abstracts 1982:195977.

*Primary Examiner*—Deborah C. Lambkin
(74) *Attorney, Agent, or Firm*—Steven D. Boyd

(57) ABSTRACT

The present invention relates to a process for the preparation of substituted alkanesulfonates by the reaction of an aqueous metal substituted 2-hydroxyethanesulfonate with a nucleophile. 2-Alkylaminoalkanesulfonate is formed when the nucleophile is an amine. The invention also relates to the optimization of reaction conditions to produce an optimum yield.

12 Claims, No Drawings

PREPARATION OF SUBSTITUTED ALKANESULFONATES FROM 2-HYDROXYALKANESULFONATES

This application claims priority of U.S. Provisional Application No. 60/503,263 filed Sep. 16, 2003.

BACKGROUND OF THE INVENTION

1. Field of the Invention

The present invention relates to a process for the preparation of substituted alkanesulfonates by the reaction of an aqueous metal substituted 2-hydroxyethanesulfonate with a nucleophile. When the nucleophile is an amine, a 2-alkylaminoalkanesulfonate is formed. The invention also relates to the optimization of reaction conditions to produce an optimum yield.

2. Description of the Prior Art

2-Alkylaminoethanesulfonates, also known as alkyltaurines, are useful raw materials for preparing certain zwitterionic 2-alkylaminoethanesulfonic acids. These 2-alkylaminoethanesulfonic acids are used as biological buffers in fermentation and medical diagnostic applications, where they offer less cytotoxicity than other buffering systems. They also have use as buffers in processes for making electronic and microelectronic devices. Some useful 2-alkylaminoethanesulfonic acids include 2-(4-(2-hydroxyethyl)piperazin-1-yl)-ethanesulfonic acid [HEPES], 2-(morpholin-4-yl)ethanesulfonic acid [MES], piperazine-1,4-bis(2-ethanesulfonic acid) [PIPES], 2-(bis(2-hydroxyethyl)amino) ethanesulfonic acid [BES], 2-((2-hydroxy-1,1-bis(hydroxymethyl)ethyl)-amino)ethanesulfonic acid [TES], 2-(cyclohexylamino) ethanesulfonic acid [CHES], and 2-(pyridinium-1-) ethanesulfonate.

2-Alkylaminoethanesulfonates have been prepared using a number of raw materials and processes. Preparation of 2-alkylaminoethanesulfonates such as sodium methylaminoethanesulfonate, HEPES, MES, PIPES, and BES by reaction of an amine and a 2-haloalkanesulfonate, with in-situ alkaline neutralization of the by-product amine hydrohalides, has been disclosed in East German Patent 15289, *Biochemistry*, Vol. 5, pp 467–477, 1966, Chapter 3 of *Photosynthesis*, A San Pietro, Ed., *Methods in Enzymology*, Vol. 23–24,69, pp 53–68, 1971, and *Shengwu Huaxue Yu Shenwu Wuli Jinzhan*, Vol. 37, pp 44–46, 1981 (*Chemical Abstacts* 1982:195977). Preparation of hydroxy-substituted aminopropanesulfonates from amines and sodium 3-chloro-2-hydroxypropanesulfonate is disclosed in U.S. Pat. Nos. 4,169,950 and 4,246,194. Related preparations using amines and carbyl sulfate are disclosed in WO 99/41236.

Processes to prepare 2-alkylaminoethanesulfonates from amines and various vinylsulfonates have also been disclosed. These include preparations using sodium vinylsulfonate in U.S. Pat. No. 4,481,150, and U.S. Pat. No. 4,582,651; preparations from vinylsulfonate esters in German Patent 1,151,149; French Patent 2,041,439; and French Patent 2,270,241; and preparations from vinylsulfonyl chloride in French Patent 1,529,883.

None of the above references describe the use of the 2-hydroxyalkylsulfonate metal salts as a raw material. 2-Hydroxyalkylsulfonates salts are generally less expensive than the raw materials of the above cited references. 2-Hydroxyalkanesulfonates can be reacted with amines to produce 2-alkylaminoalkanesulfonates. British Patent 1,381,828 discloses the reaction of equimolar amounts of anhydrous sodium 2-hydroxyethanesulfonate with primary hydroxyalkyl- or alkoxyalkylamines at 180–220° C. in a sealed autoclave. The product purities were low (92–94%), while a nominally stoichiometric yield of by-product water was obtained, probably due to further reaction of the formed products, which are secondary amines, with the sodium 2-hydroxyalkanesulfonate raw material to form tertiary amine impurities. British Patent 1,503,280, discloses the reaction of di- and polyamines with anhydrous sodium 2-hydroxyethanesufonate, the latter being charged at substoichiometric or stoichiometric quantities of 0.125–1.0 molar equivalents, relative to the amount of N—H functionality in the amine raw materials. In one embodiment, the reaction was conducted in a stepwise manner by heating at 200–220° C. at atmospheric pressure with distillative removal of water, followed by further heating under vacuum to remove the last of the formed water. Another embodiment describes heating the reactants at 210–240° C. at 10–20 atmospheres in an autoclave with no removal of water.

U.S. Pat. No. 4,080,315 discloses a process using NaOH as a catalyst for the preparation of the sodium salt of BES by the reaction of a large excess of diethanolamine with anhydrous sodium 2-hydroxyethanesulfonate at 180–190° C./atmospheric pressure, with continuous removal of the water formed in the reaction. The excess amine was subsequently removed from the crude reaction product by distillation. Similarly, Japanese patent application JP 04/360863 discloses the preparation of sodium 2-(monoalkylamino) ethanesulfonates $RNHCH_2CH_2SO_3Na$ (R=methyl, propyl, cyclohexyl) by the reaction of anhydrous sodium 2-hydroxyethanesulfonate and the primary alkylamine in the presence of catalytic NaOH.

While water is generated as a product of the reaction of sodium 2-hydroxyalkylsufonate with amines, none of the above references describe the use of aqueous 2-hydroxyalkylsulfonate feedstocks. The aqueous feedstocks are generally less expensive and easier to handle in a manufacturing setting. References to processes using aqueous 2-hydroxyalkylsulfonate feedstocks require large excesses of amine raw materials, creating extra steps for the removal of these excess reactants from the product. The use of aqueous raw materials is disclosed in British Patent 815,167, where 2-(monoalkylamino) ethanesulfonates are prepared from sodium 2-hydroxyethane sufonate using a large excess of a monoalkylamine in water with NaOH catalyst. In this procedure, the reagents were combined and heated at 205° C. for 1.5 hours, and the product was obtained in 98 percent molar yield after distillation of the excess amine from the product mixture.

East German Patent 84,394 discloses the reaction of 50 percent aqueous sodium 2-hydroxyethanesulfonate with a ten-fold molar excess of aqueous 40 percent methylamine and a large amount of NaOH catalyst (0.37–0.89 molar equivalents) to produce sodium 2-(methylamino)ethanesulfonate. Similarly, Japanese patent application JP 07/278,097 discloses the reaction at 250° C. for 3 hours of a large excess of aqueous methylamine with aqueous sodium 2-hydroxyethanesulfonate containing less than 1 percent sulfite. There is no mention of any catalyst in this citation.

There is a need for the production of substituted alkanesulfonates from the less expensive aqueous metal substituted 2-hydroxyethanesulfonate at high yields without the need for large excesses of reactants. Surprisingly it has been found that substantially stoichiometric amounts of aqueous metal substituted 2-hydroxyethane sulfonate and nucleophilic compounds can be reacted in the presence of an alkaline catalyst to produce substituted alkanesulfonates. By controlling the reaction conditions, high yields are achieved.

SUMMARY OF THE INVENTION

It is an object of the invention to produce substituted alkanesulfonates by the reaction of aqueous metal substituted 2-hydroxyethanesulfonate with nucleophillic compounds.

It is a further objective of the invention to produce 2-alkylaminoethanesulfonates from the reaction of commercially available aqueous sodium 2-hydroxyethanesulfonate with an amine.

It is a further objective of the invention to optimize reaction conditions to obtain high reaction yields.

It is a further objective of the invention to optimize the level of water in the reaction, and removal of water from the reaction for high yields.

The objectives have been met by a method for preparing a substituted alkanesulfonate comprising reacting an aqueous metal substituted 2-hydroxyalkanesulfonate with at least one nucleophilic compound in the presence of an alkaline catalyst, wherein the mole ratio of both the 2-hydroxyalkanesulfonate and nucleophilic are from 80 to 120 percent of the stoichiometric requirement for the reaction.

The objectives have further been met by a method wherein excess water is removed from the reaction so that at the end of the reaction the reaction mass comprises from 2–20 percent by weight of water.

DETAILED DESCRIPTION OF THE INVENTION

This invention provides an improved method for the production of substituted alkanesulfonates from the reaction between aqueous metal substituted 2-hydroxyethanesulfonates and a nucleophilic compound. The invention also relates to optimization of the reaction conditions for optimum yield.

The substituted alkanesulfonates of the invention are those having the formulas

X—R—SO$_3$M, MO$_3$SR—Y—RSO$_3$M, and Z-RSO$_3$M, where R independently represents a substituted 2-hydroxyethane group; M represents a metal selected from the Group I, Group II, or transition metals; X represents an amino group of formula R$^1$R$^2$N with R$^1$ and R$^2$ independently representing hydrogen or C$_1$–C$_{20}$ linear or cyclic alkyl, alkylene, aromatic or heterocyclic groups, and may optionally be substituted; or X represents a heterocyclic-amino group of formulas

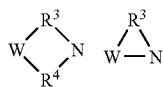

wherein R$^3$ and R$^4$ are independently C$_1$–C$_5$ alkyl or alkylene; and optionally incorporating carbonyl, sulfonyl, or sulfinyl, ether, (alkyl)amino, or carbinol functional groups, and W being selected from the group O, S, SO$_2$, CO, R$^1$—N, R$^1$—CO—N, R$^1$—SO$_2$—N, with R$^1$ being defined above; and wherein Y represents a di- or polyamine of the formula

with R$^3$ and R$^4$ being as defined above; and wherein Z represents a mercapto-, alkylthio, or alkoxy functional group of the general formulas HS, R$^6$S and R$^7$O with R$^6$ and R$^7$ representing C$_1$–C$_{20}$ linear or cyclic alkyl, alkylene, aromatic or heterocyclic groups optionally containing ether, sulfide, disulfide, polysulfide, amino, hydroxy, alkoxy, carbonyl, amide, ester or thioester functionality.

The substituted alkanesulfonate is formed by the reaction of aqueous 2-hydroxyalkanesulfonates with a nucleophilic compound as shown in one of the following reactions:

HORSO$_3$M+XH→X—RSO$_3$M+H$_2$O;  (1)

HORSO$_3$M+YH$_2$→MO$_3$SR—Y—RSO$_3$M+2H$_2$O; or  (2)

HORSO$_3$M+ZH→Z-RSO$_3$M+H$_2$O,  (3)

wherein R, M, X, Y, and Z, have the same meanings as described above.

The metal substituted 2-hydroxyalkanesulfonates useful as reactants are those in aqueous form. By aqueous form is meant that the aqueous composition contains at least 10 percent by weight of water, and preferably from 20 to 75 percent by weight of water. Substituted 2-hydroxyalkanesulfonates of the invention have the formula

HO—CHR$^8$—CH$_2$—SO$_3$M where M is as described above, and R8 is H, or optionally substituted C1–C20 linear or cyclic alkyl, alkylene, arylalkyl, aromatic or heterocyclic group. 2-Hydroxy alkanesulfonates useful in the invention include, but are not limited to 2-hydroxyethanesulfonate, 2-hydroxypropanesulfonate, 2-hydroxybutanesulfonate, 2-hydroxy-2-methylpropanesulfonate and linear or branched higher alkyl homologs. A preferred 2-hydroxyalkane sulfonate is sodium 2-hydroxyethanesulfonate, also known as sodium isethionate, which is the produced by the reaction of oxirane and sodium hydrogen sulfite in aqueous media. It is available commercially, generally having a water content of between 35 and 55 percent (45–65 percent solids). The aqueous 2-hydroxyethanesulfonate is generally less expensive than either the anhydrous solid, or the sodium haloethanesulfonates, sodium vinyl sulfonate, or sodium vinyl sulfonate esters used as the raw materials in other processes for forming substituted ethanesulfonates. Additionally, as a liquid raw material the aqueous solution is simpler and safer to handle in a manufacturing environment. The 2-hydroxyalkanesulfonate is reacted with a nucleophilic compound. The nuclephilic compound may be a mixture of nucleophilic compounds, and may be used in an anhydrous form or as an aqueous solution. Preferably the nucleophilic is an organic nucleophile, and most preferably an amine. Useful nucleophilic compounds include, but are not limited to metal hydrosulfides; H2S; C1–C12 linear and branched alkanethiols or their metal salts; morpholine; N-(2-hydroxyethyl)-piperazine; N,N-diethanolamine; morpholine, piperazine, cyclohexylamine; tris(hydroxymethyl)aminomethane; cyclohexylamine; tris(hydroxymethyl)aminomethane; and the 2-(heterocyclic ammonium) ethanesulfonate internal salts. The process of this invention could also be used to prepare aminoethanesulfonates derived from substituted or unsubstituted heterocyclic amine selected from the group: 1,2,3-triazole, pyrimidine, pyrazine, 1,2,3-triazine, 1,2,4-triazine, 1,3,5-triazine, and particularly pyridine and 2- or 3-substituted imidazoles.

The reaction occurs in the presence of an alkaline catalyst or a mixture of such catalysts. Preferred catalysts include sodium hydroxide, potassium hydroxide, calcium hydroxide, magnesium hydroxide, and mixtures thereof. The catalyst is present in the reaction at a level of 0.01 molar equivalents to 0.250 molar equivalents relative to the amount of nucleophilic reagent remaining after distillative removal of excess water, and any co-distilled nucleophilic reagent, from the reaction mixture, preferably 0.02 to 0.15 molar equivalents.

The reaction occurs in an aqueous or mixed aqueous/organic media. The amount of water is such that the final water content of the reaction mixture prior to any dilution is controlled within a range of from 2–20 percent by weight of the reaction mixture. For 2-hydroxyethanesulfonate reactions, the reaction mixture starts as a solution and becomes a homogeneous mixture with the addition of the amine. As water is removed, the reaction mixture becomes a slurry.

The invention also relates to the optimization of reaction conditions to produce an optimum yield. An optimum yield is one that is greater than 93 percent of the theorectical yield, and preferably greater than 95 percent. Reaction conditions herein are primarily defined as the critical ratios of water, catalyst, reactants, and temperature which, after removal of any excess reagents or water, affords conversion in high yield. It is also to be understood that, once the critical combinations of reactant ratios, temperatures, catalyst, and solvent have been identified which provide high conversion to the desired products, other strategies for obtaining that critical combination, as well as other strategies for removal of excess water, can readily be inferred by those skilled in the art.

It was found that the optimal reaction conditions vary according to the chemical and physical properties of the amine. In particular, amines or other nucleophiles having a high boiling point such as hydroxyethylpiperazine, or those which do not significantly co-distill with water during the stripping step, could be used in a procedure in which water was continuously distilled from the reactor, such as in procedure A described below. For amines or other nucleophiles with low boiling points such as morpholine, or those which significantly co-distill with water, a procedure must be used in which the water is distilled only after the reaction has proceeded significantly to completion. In procedure C below, the water was distilled at the end of the reaction. In procedure B, water was distilled after a significant portion of the reaction occurred, followed by additional reaction. Reducing the loss of the low-boiling amine offers advantages in terms of both raw material and waste costs.

The reaction between the aqueous 2-hydroxyalkanesulfonate and amine generally occurs at a temperature in the range of 140 to 225° C., preferably 190 to 210° C. As expected, the reaction rate increases at elevated temperatures, thereby requiring less time for full reaction. It was found that at the elevated temperatures, the reaction occurs at a much more rapid rate. While the scope of the claims is not limited by any particular theory, it is believed that at temperatures above the melting point, or the dissolution temperature, of the reaction products, the liquid environment facilitates the reaction. It was also found that, a catastrophic decrease in yield occurred in reactions using hydroxyethylpiperazine as the reactive amine when the reaction temperature was held below 150° C. While not being bound by any theory, it is believed that at these lower temperatures and water contents, the metal 2-hydroxyethanesulfonate is not sufficiently soluble in the reaction mixture to provide acceptable conversion to product.

The ratio of 2-hydroxyalkanesulfonate to amine reactants preferably is between 80 and 120 percent of the stoichiometric requirement for the reaction. In one embodiment, excess amounts of raw materials may be used such that, after any loss of raw materials to codistillation with the excess water, the molar ratio of the amine to metal 2-hydroxyalkanesulfonate, the reactants is from 80 to 120 percent of the stoichiometric requirement for the reaction.

The amount of water in the reaction is a key parameter to the optimization of the reaction. It was found that excessive amounts of water in the reaction mixture prevented the complete conversion of raw materials to products, and that above a critical water content in the reaction mixture, the molar yield of product is limited to ca. 93–95% of the theoretical amount achievable based on the stoichiometric relationships between the reactants. It was also found that the amine raw material can adversely effect the solubility of sodium 2-hydroxyethanesulfonate raw material in the reaction mixture, and that a certain minimum amount of water is needed to maintain this raw material substantially in solution or liquid phase at the reaction temperature affording a smooth conversion to product. Additionally, some amount of water found to be desirable to keep the forming 2-aminoethanesulfonate products in solution phase during the reaction. This latter amount of water may be greater than or lesser than the amount needed to maintain the sodium 2-hydroxyethanesulfonate raw material in solution phase. Moreover, all of these phenomena are strongly dependant on reaction temperature.

Commercial aqueous metal 2-hydroxyethanesulfonate generally have a water content of between 35 and 55 percent (45–65 percent solids). In that the amount of water present in the purchased metal 2-hydroxyethanesulfonate can be in excess of the desired amount of water for the reaction, it may be necessary to remove a large portion of the water by distillation.

The excess water in the reaction can be removed in several different ways so as to achieve the necessary combination of reactants and water to achieve high yield. In that the amine raw materials for the process of this invention co-distill with water to greater or lesser degrees, and that it is generally beneficial to minimize the losses of these amines during the water removal, it is necessary to adopt different water removal strategies with different amine raw materials.

Preferably, removal of excess water by distillation is done in such a way that the water content of the reaction mass upon complete conversion, and prior to any post-reaction dilutions, is from 2 to 20 percent.

In one embodiment of this invention, excess water is removed by distillation during the heating to the reaction mass to the 140–225° C. reaction temperature. This method was found to work best for amines or other nucleophiles having a high boiling, or those which do not significantly co-distill with water during the stripping step.

In that some of the raw materials may co-distill or form azeotropic mixtures with the water to be removed, another embodiment of this invention employs a partial conversion of the raw materials to product, with subsequent removal of the excess water from the reaction mass at a temperature within the 140–225° C. range. This is optionally followed by further reaction to achieve complete conversion to product, in a way that is consistent with the second embodiment.

Another embodiment of the invention, involves the concurrent continuous removal of the excess water introduced with the raw materials and conversion of the reactants to product while the reaction mass is being heated in the 140–225° C. temperature range.

Still another embodiment of the invention involves the continuous addition of any or all of the raw materials to the reaction at a temperature of 140–225° C., with continuous removal of the excess water.

In that the critical water concentrations for the reaction are low compared to the amount of water needed to keep the product in solution at lower temperatures, it is advantageous to incorporate a post-reaction addition of water or another solvent to the reaction product mixture during cooling to maintain the product mixture in solution.

In any of the above embodiments of the invention, it has been found that a convenient indicator that the appropriate amount of water has been removed from the mixture is the observed pressure at the end of the stripping step.

EXAMPLES

Procedure A

An electrically-heated, mechanically stirred 1 liter autoclave was fitted with an vent valve connected in turn to a condenser and receiver assembly, a bottom valve, a thermowell, a pressure gauge, an inlet line for feeding of reagents, and a pressure-relief valve. The receiver was placed on a balance to facilitate continuous determination of the amount of distillate collected in the receiver.

The amine starting material, aqueous sodium 2-hydroxyethanesulfonate, and aqueous 50 percent sodium hydroxide were charged to the autoclave. With the isolation valve open, the reaction mixture was rapidly heated with stirring until condensate was detected in the condenser/receiver. The mixture was further heated with continuous removal of water until the targeted amount of distillate had been removed. An analysis of the collected aqueous distillate was performed by UV spectroscopy to determine the amount of amine which co-distilled with the water. The isolation valve was then closed and the reaction mixture further heated to a target temperature in the range of 140–200° C. for 2–17 hours as specified in Examples 1–8. The reaction mixture was then cooled until the pressure dropped to 0 psig (ca. 110° C.) whereupon dilution water was added to dilute the concentrated reaction product. The resulting solution was then cooled to room temperature and drained from the reactor. Analysis of the product mixture was then performed by various chromatographic and spectroscopic procedures as indicated in the specific examples.

Procedure B

Using the reaction vessel described in Procedure A, the amine starting material, aqueous sodium 2-hydroxyethanesulfonate, and aqueous 50 percent sodium hydroxide were charged to the autoclave. With the isolation valve closed, the stirred reaction mixture was rapidly heated to the target reaction temperature and held at that temperature for the times specified in Example 12. The isolation valve was then carefully opened and water vapor removed from the mixture until the targeted amount of distillate had been removed. An analysis of the collected aqueous distillate was performed by UV spectroscopy to determine the amount of amine which co-distilled with the water. The isolation valve was then closed and the reaction mixture further heated to a target temperature at the target temperature for an additional 2 hours. The reaction mixture was then cooled and diluted as described in Procedure A.

Procedure C

A magnetically-stirred 70-mL fluoropolymer-lined steel autoclave was fitted with an internal thermocouple capable of determining the temperature of the liquid phase contained in the vessel, a pressure gauge, a pressure-relief valve, and a vent valve. The amine starting material, anhydrous or aqueous sodium 2-hydroxyethanesulfonate, and anhydrous or aqueous sodium hydroxide were charged to the open autoclave, which was then assembled and immersed in an electrically heated oil bath. With the vent valve closed, the stirred reaction mixture was rapidly heated to the reaction temperature and held at that temperature for the times specified in Examples 9, 10, and 13 below. The reaction mixture was then cooled to ambient temperature, the reactor opened, and the reaction product taken up in sufficient water to dissolve all solids.

Procedure D

The reactor assembly described in Procedure C was connected to an overhead condenser and receiver assembly. The amine starting material, anhydrous or aqueous sodium 2-hydroxyethanesulfonate, and anhydrous or aqueous sodium hydroxide were charged to the open autoclave, which was then assembled and immersed in an electrically heated oil bath. With the vent valve closed, the stirred reaction mixture was rapidly heated to the reaction temperature and held at that temperature for the times specified in Example 11 below. A fixed portion of water was then removed as steam in a manner similar to Procedure B. The reactor was further heated as indicated below, then cooled to ambient temperature. The reactor was then opened, and the reaction product taken up in sufficient water to dissolve all solids.

TABLE 1

| | | | Example | | | | |
|---|---|---|---|---|---|---|---|
| | | | 1 | 2 (comp) | 3 | 4 (comp) | 5 (comp) |
| Product | | | HEPES-Na | HEPES-Na | HEPES-Na | HEPES-Na | HEPES-Na |
| Procedure | | | A | A | A | A | A |
| Amine | | | HEP | HEP | HEP | HEP | HEP |
| | | charge, grams | 284.6 | 270.1 | 270.0 | 284.1 | 271.0 |
| | | charge, moles | 2.186 | 2.075 | 2.075 | 2.182 | 2.081 |
| SHES | | concentration (%) | 57.2 | 57.2 | 57.2 | 57.2 | 57.2 |
| | | charge, grams | 564.1 | 537.6 | 537.0 | 563.1 | 563.1 |
| | | charge, moles | 2.178 | 2.076 | 2.074 | 2.175 | 2.174 |
| NaOH | | concentration (%) | 50 | 50 | 50 | 50 | 50 |
| | | charge, grams | 17.0 | 8.6 | 17.0 | 17.0 | 8.51 |
| | | charge, moles | 0.212 | 0.108 | 0.212 | 0.212 | 0.106 |
| Initial | | Temperature, ° C. | Not | Not | Not | Not | Not |
| Reaction | | Max. Pressure, psig | Applicable | Applicable | Applicable | Applicable | Applicable |
| | | Hold Time, hours | | | | | |

TABLE 1-continued

| | | Example | | | | |
|---|---|---|---|---|---|---|
| | | 1 | 2 (comp) | 3 | 4 (comp) | 5 (comp) |
| Strip | Temperature, ° C. | 110–130 | 110–130 | 110–130 | 110–130 | 110–130 |
| | Distillate, grams | 167 | 153.0 | 156.1 | 164.6 | 160.0 |
| | Amine concentration, % | 1.74 | not detm. | 1.84 | 1.73 | 1.61 |
| Reaction | Temperature, ° C. | 200 | 175 | 150 | 145 | 140 |
| | Max. Pressure, psig | 68 | 36 | 16 | 16 | 16 |
| | Hold Time, hours | 2 | 7 | 17 | 17 | 17 |
| Nominal water content in stripped reaction mixture, % | | 12.3 | 12.3 | 12.7 | 12.5 | 12.5 |
| Theoretical water content (%) in reaction product mixture assuming 100% conversion | | 17.5 | 17.9 | 18.3 | 18.1 | 17.7 |
| Dilution water | grams | 259.1 | 240.9 | 240.9 | 257.8 | 240.8 |
| Product Solution | grams | 957.0 | 888.1 | 869.3 | 934.9 | 877.2 |
| Product (% in solution) | | 58.8 | 56.6 | 61.1 | 15.8 | 3.8 |
| Product (%, excluding water) | | 94.7 | 94.8 | 94.9 | 27.3 | 5.7 |
| SHES (%, excluding water) | | 1.1 | 2.2 | 0.7 | 36.2 | 46.9 |
| Amine (%, excluding water) | | 1.8 | 1.7 | 1.9 | 34.0 | 45.2 |
| Molar Yield for Product (%) | | 99.9 | <93 | 98.4 | 26 | 6 |

TABLE 2

| | | Example | | | | |
|---|---|---|---|---|---|---|
| | | 6 | 7 | 8 | 9 | 10 (comp) |
| Product | | HEPES-Na | HEPES-Na | HEPES-Na | HEPES-Na | HEPES-Na |
| Procedure | | A | A | A | C | C |
| Amine | | HEP | HEP | HEP | HEP | HEP |
| | grams | 270.0 | 271.0 | 284.2 | 25.00 | 22.05 |
| | moles | 2.073 | 2.082 | 2.183 | 0.1921 | 0.1694 |
| SHES | concentration (%) | 57.2 | 57.2 | 57.2 | 57.2 | 100 |
| | grams | 536.1 | 537.0 | 563.8 | 50 | 24.97 |
| | moles | 2.070 | 2.074 | 2.177 | 0.1931 | 0.1686 |
| NaOH | concentration (%) | 50 | 50 | 50 | 100 | 100 |
| | grams | 17.0 | 17.0 | 17.0 | 1 | 0.07 |
| | moles | 0.212 | 0.212 | 0.212 | 0.025 | 0.0018 |
| Initial | Temperature, ° C. | | | | | |
| Reaction | Max. Pressure, psig | Not | Not | Not | Not | Not |
| | Hold Time, hours | Applicable | Applicable | Applicable | Applicable | Applicable |
| Strip | Temperature, ° C. | 110–130 | 110–130 | Not | Not | Not |
| | Distillate, grams | 171.4 | 143.8 | Applicable | Applicable | Applicable |
| | Amine concentration, % | 2.26 | 1.53 | | | |
| Final | Temperature, ° C. | 150 | 150 | 151 | 175 | 204 |
| Reaction | Max. Pressure, psig | 16 | 16 | 28 | 90 | 78 |
| | Hold Time, hours | 17 | 17 | 72 | 17 | 2.25 |
| Nominal water content in stripped reaction mixture, % | | 10.8 | 14.2 | 28.9 | 28.1 | 0 |
| Theoretical water content (%) in reaction product mixture assuming 100% conversion | | 16.2 | 19.7 | 33.4 | 32.7 | 6.45 |
| Dilution water | grams | 239.0 | 240.0 | 95.0 | 0 | 71.5 |
| Product Solution | grams | 887.2 | 887.2 | 959.0 | 76.0 | not detm. (ca. 118.6) |
| Product (% in solution) | | 55.2 | 57.8 | 55.7 | 62.2 | 35.0 |
| Product (%, excluding water) | | 93.0 | 95.0 | 93.4 | 92.6 | 95.2 |
| SHES (%, excluding water) | | 0.4 | 1.0 | 1.6 | 1.9 | 1.9 |
| Amine (%, excluding water) | | 4.0 | 1.5 | 2.5 | 2.5 | 2.5 |
| Molar Yield for Product (%) | | 96.0 | 95.4 | 94.3 | 94.5 | 94.6 |

TABLE 3

| | | Example | | |
|---|---|---|---|---|
| | | 11 (comp) | 12 | 13 |
| Product | | MES-Na | MES-Na | MES-Na |
| Procedure | | D | B | C |
| Amine | | Morpholine | Morpholine | Morpholine |
| | grams | 19.36 | 248.0 | 9.38 |
| | moles | 0.2222 | 2.846 | 0.1077 |

TABLE 3-continued

| | | Example | | |
|---|---|---|---|---|
| | | 11 (comp) | 12 | 13 |
| SHES | concentration (%) | 56.7 | 56.7 | 56.7 |
| | grams | 56.40 | 660.0 | 28.20 |
| | moles | 0.2159 | 2.527 | 0.1080 |
| NaOH | concentration (%) | 50.0 | 50 | 50 |
| | grams | 0.42 | 4.86 | 0.47 |
| | moles | 0.0052 | 0.212 | 0.0052 |
| Initial Reaction | Temperature, ° C. | | 200 | |
| | Max. Pressure, psig | Not | 150 | Not |
| | Hold Time, hours | Applicable | 2 | Applicable |
| Strip | Temperature, ° C. | 100 | 200 | |
| | Distillate, grams | 19.77 | 279.4 | Not |
| | Amine concentration, % | 52.2 | 14.0 | Applicable |
| Final Reaction | Temperature, ° C. | 200 | 200 | 200 |
| | Max. Pressure, psig | 78 | 50 | 150 |
| | Hold Time, hours | 2 | 2 | 2 |
| Nominal water content in stripped reaction mixture, % | | 26.9 | 7.6 | 32.7 |
| Theoretical water content (%) in reaction product mixture assuming 100% conversion | | 28.4 | 15.6 | 37.5 |
| Dilution water | grams | 70.0 | 742 | 68.8 |
| Product Solution | grams | not detm. (ca. 126) | 1375 | not detm. (ca. 91.7) |
| Product (% in solution) | | 7.9 | 44.3 | 24.20 |
| Product (%, excluding water) | | 47.7 | 95.5 | 85.3 |
| SHES (%, excluding water) | | 48.0 | 3.5 | 9.9 |
| Amine (%, excluding water) | | 3.3 | 0.56 | 3.9 |
| Molar Yield for Product (%) | | ca. 44.2 | 98.6 | ca. 94.8 |

Key:
SHES Sodium 2-Hydroxyethanesulfonate, formula weight 148.11
HEP 4-(2-Hydroxyethyl)piperazine, formula weight 130.19
SAES Sodium 2-aminoethanesulfonate
HEPES-Na Sodium (4-(2-hydroxyethyl)piperazin-1-yl)ethanesulfonate, formula weight 260.29
MES-Na Sodium 2-(morpholin-4-yl)ethanesulfonate, formula weight 217.16
Notes
Product analyses by ion chromatography or $^1$H-Nuclear Magnetic Resonance
Amine content in distillates determined by UV absorption @ 210 nm
not detm. = not determined The effect of temperature on the molar yield of product is readily apparent when one compares the results described in Examples 1, 3, and 4. In these Examples where hydroxyethylpiperazine was employed as the reactive amine, a catastrophic decrease in yield was observed when the reaction temperature was held below 150° C.

The inhibitory effects on molar yield of high water content in the reaction mixture is readily apparent when one compares the results from Examples 3, 7 and 8, all performed at 150° C. reaction temperatures using hydroxyethylpiperazine as the amine raw material. Looking at the theoretical water content of the reaction product mixtures assuming complete conversion in Examples 3 and 7, as the theoretical water content increased from 18.3% and 19.7%, the molar yields decreased from 98.4% to 95.4% after 17 hours at 150° C. At very high water contents, e.g., 33.4% in Example 8, the yield further decreased to ca. 94.3%.

A similar effect is apparent upon comparison of Examples 12 and 13, both using morpholine as raw material and 200° C. reaction temperature, where the molar yield decreased from 98.6% to ca. 94.8% as the theoretical water content assuming complete conversion decreased from 37.5% to 15.6%.

The impact of insufficient water in the reaction mixture can be seen by comparing Examples 1, 6, and 10, all performed at 200–204° C. using hydroxyethylpiperazine as the amine. As the theoretical water content, assuming 100% conversion, decreased from 17.5% to 16.2% and finally 6.45%, there was a corresponding decrease in molar yield from 99.9% to 96.0% and finally 94.6%.

The effect of temperature on the molar yield of product is readily apparent when one compares the results described in Examples 1, 3, and 4. In these cases where hydroxyethylpiperazine was employed as the reactive amine, a catastrophic decrease in yield was observed when the reaction temperature was held below 150° C. At these temperatures and water contents, the metal 2-hydroxyethanesulfonate is not sufficiently soluble in the reaction mixture to provide acceptable conversion to product.

What is claimed is:

1. A method for preparing a substituted alkanesulfonate comprising reacting an aqueous metal substituted 2-hydroxyalkanesulfonate with at least one nucleophilic compound in the presence of an alkaline catalyst, wherein the mole ratio of both the 2-hydroxyalkanesulfonate and nucleophilic are from 80 to 120 percent of the stoichiometric requirement for the reaction.

2. The method of claim 1 wherein said nucleophilic compound is an amine.

3. The method of claim 2 wherein said amine is selected from group consisting of morpholine, N-(2-hydroxyethyl)-piperazine, N,N-diethanol amine, cyclohexylamine, and tris (hydroxymethyl)aminomethane.

4. The method of claim 1 wherein said aqueous substituted 2-hydroxyalkanesulfonate comprises sodium 2-hydroxyethanesulfonate.

5. The method of claim 4 wherein said aqueous sodium 2-hydroxyethanesulfonate comprises from 35 to 65 percent by weight of water.

6. The method of claim 1 wherein said reaction occurs at a temperature of from 140° C. to 225° C.

7. The method of claim 1 wherein some or all raw materials are added to the reaction on a continuous basis while continuous removal of water occurs.

8. The method of claim 1 wherein said nucleophile is selected from the group consisting of metal hydrosulfides, hydrogensulfide, $C_1$–$C_{12}$ linear or branched alkanethiols, and the metal salts thereof.

9. The method of claim 1 wherein excess water is removed from the reaction so that at the end of the reaction the reaction mass comprises from 2–20 percent by weight of water.

10. The method of claim 9 wherein said water removal comprises distillative removal of water as the reaction mass is heated to a temperature of between 140–225° C.

11. The method of claim 9 wherein the water removal from the reaction mass occurs after partial conversion to product, followed by further reaction of the remaining reactants.

12. The method of claim 9 wherein water is removed continuously during the reaction.

* * * * *